(12) United States Patent
Sahota

(10) Patent No.: US 7,241,284 B2
(45) Date of Patent: Jul. 10, 2007

(54) METHOD OF INHIBITING RESTENOSIS

(76) Inventor: Harvinder Sahota, 3861 Wisteria, Seal Beach, CA (US) 90740

( * ) Notice: Subject to any disclaimer, the term of this patent is extended or adjusted under 35 U.S.C. 154(b) by 176 days.

(21) Appl. No.: 10/207,411

(22) Filed: Jul. 26, 2002

(65) Prior Publication Data

US 2004/0018113 A1    Jan. 29, 2004

(51) Int. Cl.
*A61M 31/00* (2006.01)
*A61F 2/06* (2006.01)

(52) U.S. Cl. ..................... 604/507; 623/1.11

(58) Field of Classification Search ........ 604/507–509, 604/28, 29, 194, 195; 623/1.15, 1.48, 1.11; 606/194, 195
See application file for complete search history.

(56) References Cited

U.S. PATENT DOCUMENTS

| | | | | |
|---|---|---|---|---|
| 4,620,846 A | * | 11/1986 | Goldberg et al. | 604/28 |
| 5,224,939 A | * | 7/1993 | Holman et al. | 604/528 |
| 5,370,608 A | * | 12/1994 | Sahota et al. | 606/194 |
| 5,554,182 A | * | 9/1996 | Dinh et al. | 623/1.48 |
| 5,562,944 A | * | 10/1996 | Kafrawy | 427/156 |
| 5,571,166 A | * | 11/1996 | Dinh et al. | 623/1.15 |
| 5,688,475 A | * | 11/1997 | Duthie, Jr. | 422/186.3 |
| 6,329,081 B1 | * | 12/2001 | Fudanoki et al. | 428/687 |
| 6,646,241 B1 | * | 11/2003 | Varma et al. | 219/679 |

OTHER PUBLICATIONS

Infect Control Hosp Epidemiol. Nosocomial infection rates for interhospital comparison: limitations and possible solutions. A Report from the National Nosocomial Infections Surveillance (NNIS) System. Oct. 12, 1991(10):609-21.*
Hans H. Schicht, "The Use of Clean-Room Technology in Medical Device Manufacturing: A Tool in the Service of Quality, Part I," Medical Device Technology, 5(2), 22-25 (1993).*
Hans H. Schicht, "The Use of Clean-Room Technology in Medical Device Manufacturing: A Tool in the Service of Quality, Part II," Medical Device Technology, 5(4), 18-19 (1994).*
Satyavan Sharma et al., "Current Management of Saphenous Vein Graft Disease," The Internet Journal of Cardiology, 2(2), ISSN: 1528-834X, (2004).*

* cited by examiner

*Primary Examiner*—Sharon E. Kennedy
(74) *Attorney, Agent, or Firm*—Knobbe Martens Olson & Bear LLP

(57) ABSTRACT

A method of inhibiting restenosis is disclosed. The method includes reducing contaminants during manufacturing of angioplasty devices and during angioplasty procedures. An angioplasty device is preferably examined for contaminants prior to the angioplasty procedure, and the contaminants are reduce if present.

10 Claims, 1 Drawing Sheet

METHOD OF INHIBITING RESTENOSIS

BACKGROUND OF THE INVENTION

1. Field of the Invention

The present invention relates to medical procedures and, in particular a method for inhibiting restenosis through improved manufacturing techniques for angioplasty catheters, and improved procedure techniques.

2. Description of the Related Art

The cause of restenosis in angioplasty has been a mystery to health care professionals. Many diseases cause body lumens to undergo stenosis or a narrowing of a canal within the body. The resulting reduced blood flow can permanently damage tissue and organs. Stenotic regions that limit or obstruct coronary blood flow are the major cause of ischemic heart disease related mortality and result in 500,000–600,000 deaths in the United States annually.

The therapeutic alternatives available for treatment of stenosis include intervention (alone or in combination of therapeutic agents) to remove the blockage, replacement of the blocked segment with a new segment of artery, or the use of catheter-mounted devices such as a balloon catheter to dilate the artery. The dilation of an artery with a balloon catheter is called percutaneous transluminal angioplasty (PTA). During angioplasty, a balloon catheter in a deflated state is inserted within a stenotic segment of a blood vessel and is inflated and deflated a number of times to expand the vessel. A stent may also be delivered, as know in the art.

Often angioplasty permanently opens previously occluded blood vessels; however, restenosis, thrombosis, or vessel collapse may occur following angioplasty. A major difficulty with PTA is the problem of post-angioplasty closure of the vessel, both immediately after PTA (acute reocclusion) and in the long term (restenosis). Recently, intravascular stents have been examined as a means of preventing acute reclosure after PTA.

Restenosis refers to the re-narrowing of an artery after an initially successful angioplasty due to exaggerated healing which causes a proliferation of tissue in the angioplasty area. Thrombosis is a clotting within a blood vessel that may cause infarction of tissues supplied by the blood vessel.

Re-narrowing (restenosis) of an artery after angioplasty occurs in 10–50% of patients undergoing this procedure and subsequently requires either further angioplasty or more invasive surgical procedures. While the exact processes promoting restenosis are still under investigation, the process of PTA is believed to injure resident arterial endothelium and smooth muscle cells (SMC). In response to this injury, adhering platelets, infiltrating macrophages, leukocytes, or the smooth muscle cells (SMC) themselves release cell derived growth factors.

Restenosis (chronic reclosure) after angioplasty is a more gradual process than acute reocclusion: 30% of patients with subtotal lesions and 50% of patients with chronic total lesions will go on to restenosis after angioplasty.

Because 30–50% of patients undergoing PTCA will experience restenosis, restenosis has clearly limited the success of PTCA as a therapeutic approach to coronary artery disease. Because SMC proliferation and migration are intimately involved with the pathophysiological response to arterial injury, prevention of SMC proliferation and migration represents a target for pharmacological intervention in the prevention of restenosis.

In order to prevent restenosis and vessel collapse, stents of various configurations have been used to hold the lumen of a blood vessel open following angioplasty. Stents do not entirely reduce the occurrence of thrombotic abrupt closure due to clotting; stents with rough surfaces exposed to blood flow may actually increase thrombosis, and restenosis may still occur because tissue may grow through and around the stent and the lattice of the stent.

A method of reducing the factors causing restenosis and of inhibiting restenosis is required.

SUMMARY OF THE INVENTION

Procedures for inhibiting restenosis are disclosed. The procedures are directed to reducing contaminants during the manufacture of angioplasty catheters and during angioplasty procedures. In accordance with one procedure, angioplasty devices, such as catheters, wires, stents and the like are manufactured in a clean-room environment, such as those used in processing semiconductors, to minimize or eliminate contaminants. In addition, contaminants may be minimized using proper precautions during procedures.

The contaminants may include glove material residue, glove powder, sterilizing materials or residue, gauze residue, chemicals, dust, saline, minerals and combinations thereof. These contaminants may be reduced by using different gloves, sterilizing materials, gauze or chemicals, using only distilled water during procedures instead of saline and even by performing procedure in a clean room or clean room like environment. Contaminants from the manufacturing process may be reduced by manufacturing in clean room environments. In addition, during sterilization procedures, care is taken to not utilize chemicals that contribute to restenosis.

In addition, interventional cardiology procedures may be performed by eliminating the use of treatment chemicals and drugs, and/or eliminating their introduction directly to the treatment site, which are found to contribute to restenosis.

DETAILED DESCRIPTION OF THE PREFERRED EMBODIMENT

Figure 1:
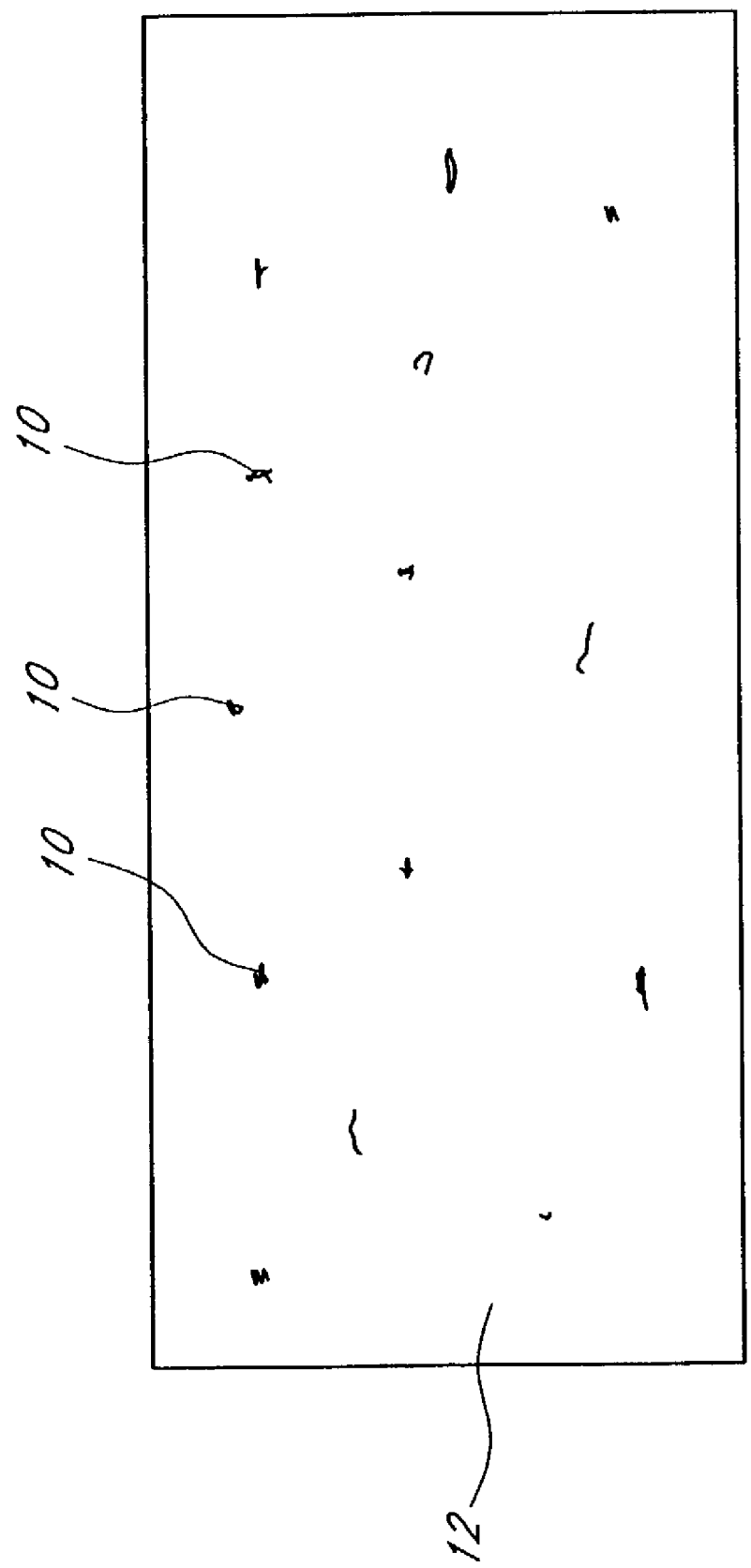
FIG. 1 is a schematic view of an exemplary microscopic view of an angioplasty device with foreign bodies present.

The following detailed description presents various specific embodiments of the present invention. However, such embodiments are illustrative of the invention and do not restrict the invention. A multitude of different forms is possible, and the invention is defined by the claims with the claim terms used in their ordinary and accustomed meaning. In this description, reference is made to the drawings wherein like parts are designated with like numerals.

Methods of inhibiting restenosis are disclosed, which focus on reducing contaminants introduced during an angioplasty procedure. With reference to FIG. 1, contaminants 10 and stent structure 12 are shown in a simplified schematic drawing. Applicant has observed that contaminants or foreign bodies 10 are present on a stent structure 12 prior to implantation, as used in an angioplasty procedure. Similar impurities are found on other interventional cardiology devices, such as catheters and wires used during procedures. The FIGURE represents an illustration of what is seen through an electron microscope. Although some impurities are visible using conventional optical microscopy, many are not generally visible to the human eye, or even with a conventional optical microscope. Thus, during procedures, an electron microscope is advantageous to examiner devices to confirm they are free of impurities. Alternatively, or similarly, an electron microscope may be used in the inspection of devices at the time of manufacture to confirm the substantial absence of impurities.

These contaminants may include residue from gloves, powder in gloves, sterilizing material, chemicals used during the procedure, materials used to make the balloon, stent, and catheters, and other matter collected on the angioplasty device during the manufacture or handling. Other contaminants or foreign bodies may found on a stent as can be determined through routine experimentation.

The methods of preventing restenosis include manufacturing the angioplasty devices in an environment that minimizes contaminants, such as in a clean room environment as used in processing integrated circuits. In addition, an improved procedure for completing an angioplasty procedure involves handling the angioplasty device in a manner to minimize introducing even microscopic contaminants into the arteries. The latter method includes using a different material, with no residue or contaminants, to make gloves, using different chemicals during the procedure, using powder free gloves, using chemical free gloves, using an angioplasty device made in a clean-room, using completely inert materials during the procedure, and performing the angioplasty in a contaminant-free environment, such as a clean room, using different methods of sterilization that do not introduce contaminants, such as sterilization in a clean-room environment, using different materials to build balloons and catheters and different techniques for handling gauze and gloves. As additional sources of the contamination are determined through experimentation by those of skill in the art, additional methods of reducing contamination will be apparent those of skill in the art, and are within the scope of this invention.

As the contaminants can not always be seen by eye, an electron microscope is preferably used to determine if contaminants are present prior to insertion of any device into the arteries. If contaminants are present, then procedures that do not introduce new contaminants may be used, such as washing in contaminant-free saline solution, or preferably, distilled water. Saline solution contains saline, which is an impurity itself Thus, distilled water is preferable, in that it is more free of impurities.

In addition, interventional cardiology procedures may be performed by eliminating the use of treatment chemicals and drugs that are found to contribute to restenosis, and/or eliminating their introduction directly to the treatment site.

Although the present invention has been described in terms of certain preferred embodiments, other embodiments of the invention including variations in dimensions, configuration and materials will be apparent to those of skill in the art in view of the disclosure herein. In addition, all features discussed in connection with any one embodiments herein can be readily adapted for use in other embodiments herein. The use of different terms or reference numerals for similar features in different embodiments does not imply differences other than those which may be expressly set forth. Accordingly, the present invention is intended to be defined solely by reference to the appended claims, and not limited to the preferred embodiments disclosed herein.

What is claimed is:

1. A method of inhibiting restenosis, comprising:
   manufacturing an angioplasty device, for insertion in a vessel of a patient, in a clean-room environment; and
   inspecting the angioplasty device for non-living particulate contaminants prior to performing a medical procedure and determining if said contaminants are present on said device by examining the angioplasty device using an electron microscope.

2. A method of inhibiting restenosis, comprising:
   sterilizing an angioplasty device;
   examining the angioplasty device with an electron microscope for particulate contaminants remaining on the angioplasty device after the step of sterilizing the angioplasty device;
   reducing the particulate contaminants prior to an angioplasty procedure; and
   performing an angioplasty procedure with said angioplasty device after the step of reducing the particulate contaminants.

3. The method of claim 2, wherein the step of reducing comprises utilizing reduced contaminant gloves.

4. The method of claim 2, wherein the step of reducing comprising performing said angioplasty procedure in a reduced-contaminant environment.

5. The method of claim 4, wherein the reduced contaminant environment comprises a clean-room environment.

6. The method of claim 2, wherein the particulate contaminants are selected from the group consisting of materials to make gloves, chemicals, sterilization residue, powder, and dust.

7. A method of inhibiting restenosis, comprising:
   sterilizing an angioplasty device;
   examining the angioplasty device for particulate contaminants remaining on the angioplasty device after the step of sterilizing the angioplasty device;
   reducing the particulate contaminants prior to an angioplasty procedure; and
   performing an angioplasty procedure with said angioplasty device in a clean-room environment after the step of reducing the particulate contaminants.

8. The method of claim 7, wherein the step of examining comprises examining the angioplasty device using an electron microscope.

9. The method of claim 7, wherein the step of reducing comprising utilizing reduced contaminant gloves.

10. The method of claim 7, wherein the particulate contaminants are selected from the group consisting of materials to make gloves, chemicals, sterilization residue, powder, and dust.

* * * * *